(12) United States Patent
Ruat et al.

(10) Patent No.: US 7,084,167 B2
(45) Date of Patent: Aug. 1, 2006

(54) CALCIUM RECEPTOR ACTIVE MOLECULES AND METHOD FOR PREPARING SAME

(75) Inventors: Martial Ruat, Bourg la Reine (FR); Robert Dodd, Paris (FR); Hélène Véronique Faure, Gif-sur-Yvette (FR); Philippe Marcel Dauban, Bures-sur-Yvette (FR); Albane Kessler, Paris (FR); Pierre Jean-Paul Potier, Paris (FR)

(73) Assignee: Centre National de la Rechereche Scientifique (CNRS), Cedex (FR)

( * ) Notice: Subject to any disclaimer, the term of this patent is extended or adjusted under 35 U.S.C. 154(b) by 324 days.

(21) Appl. No.: 10/296,288

(22) PCT Filed: May 23, 2001

(86) PCT No.: PCT/FR01/01599

§ 371 (c)(1),
(2), (4) Date: Apr. 24, 2003

(87) PCT Pub. No.: WO01/90069

PCT Pub. Date: Nov. 29, 2001

(65) Prior Publication Data

US 2003/0199497 A1    Oct. 23, 2003

(30) Foreign Application Priority Data

May 24, 2000  (FR) .................................. 00 06619

(51) Int. Cl.
*A61K 31/404* (2006.01)
*A61K 31/4045* (2006.01)
*C07D 209/04* (2006.01)
*C07D 209/10* (2006.01)

(52) U.S. Cl. ...................... 514/415; 514/418; 548/484; 548/491; 548/504

(58) Field of Classification Search ...................... None
See application file for complete search history.

(56) References Cited

U.S. PATENT DOCUMENTS 3,906,099 A    9/1975  Morrison et al.

FOREIGN PATENT DOCUMENTS

| ES | 542696 | 4/1985 |
|---|---|---|
| ES | 2010406 | 1/1989 |
| WO | WO 93/04373 | 3/1993 |
| WO | WO 96/12697 | 5/1996 |
| WO | WO 96/23789 | 8/1996 |
| WO | WO 00/21910 | 4/2000 |
| WO | WO 00/32578 | 6/2000 |
| WO | WO 00/35864 | 6/2000 |
| WO | WO 01/34562 | 5/2002 |

OTHER PUBLICATIONS

Cruces, et al., "Acetylenic and Allenic Derivatives of 2-(1-methylindolyl)methylamine As Selective Inhibitors of the Monoamine Oxidases A and B," Farmaco, Edizione Scientifica, vol. 43, Iss. 7-8, p. 567-73 (1988).*

Cherqaoui et al.; Structure-selectivity relationship of MAO inhibitors using neural networks; Models in Chemistry 135 (1-2), pp. 79-91 (1998).

Ferry et al.; Effects of divalent cations and of a calcimimetic on adrenocorticotropic hormone release in pituitary cells, Biochem. and Biophys. Res. Comm. 238, pp. 866-873 (1997).

Nemeth et al.; Calcimimetic compounds: a direct approach to controlling plasma levels of parathyroid hormone in hyperparathyroidism, TEM, vol. 10, No. 9, pp. 66-71 (1999).

Ye et al.; Amyloid-62 proteins activate $CA^{2+}$ permeable channels through calcium-sensing receptors, J. Neuroscience Res. 47:547-554 (1997).

Antonsen et al.; A cacimimetic agent acutely suppresses parathyroid hormone levels in patients with chronic renal failure; Kidney International, 53:223-227 (1998).

(Continued)

*Primary Examiner*—Kamal A. Saeed
*Assistant Examiner*—Andrew B. Freistein
(74) *Attorney, Agent, or Firm*—Foley & Lardner LLP

(57) ABSTRACT

The invention concerns compounds of general formula (I) wherein: the group X represents a —NR4, —CH═N or —CHR5-NR4-group; the group Y represents an oxygen or sulphur atom or a NR, —CR5, —CHR5-, —CR5═CR6- or —CHR5-CHR6 group provided that when group X represents the —CH═N— or —CHR5-NR4-group, group Y represents an oxygen or a sulphur atom or a Nr, —CR5 or —CHR group; the group R represents a hydrogen atom or an alkyl, aryl or aralkyl group; the groups R1, R5 and R6, identical or different, represent each a hydrogen or halogen atom or an alkyl or alkoxy group; the group R2 represents a hydrogen atom or an alkyl group; the group R3 represents an aryl group; and the group R4 represents a hydrogen atom, an alkyl, aryl, aralkyl, alkylsulphonamide, arylsulphonamide or aralkylsulphonamide group; and their salt with a pharmaceutically acceptable acid, in the form of a racemic mixture and their optically pure isomer. The invention also concerns their preparation, pharmaceutical compositions containing them and their use as CaSR activity modulator and as medicine for preferably treating diseases or physiological disorders involving the intervention of CaSR activity modulation.

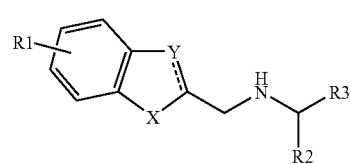

9 Claims, No Drawings

OTHER PUBLICATIONS

Wada et al.; NPS R-568 halts or reverses osteitis fibrosa I uremic rats; Kidney International 53:448-453 (1998).

Wada et al.; The calcimimetic compound NPS R-568 suppresses parathyroid cell proliferation in rats with renal insufficiency; INIST CNRS 2977-2983 (2002).

Silverberg et al.; Short-term inhibition of parathyroid hormone secretion by a calcium receptor agonist in patients with primary hyperparathyroidism, New England Journal of Medicine, 1506-1510 (1997).

Brown et al.; The extracellular calcium-sensing receptor: Its role in health and disease; Annu. Rev. Med. 49:15-29 (1998).

Brown et al.; Cloning and characterization of an extracellular CA2+ sensing receptor from bovine parathyroid; Nature 366:575-580 (1993).

Nemeth et al.; Calcimimetics with potent and selective activity on the parathyroid calcium receptor, PNAS 95:4040-4045 (1998).

Pollak et al.; Autosomal dominant hypocalcaemia caused by a CA2+ sensing receptor gene mutation, Nature Genetics, 8:303-307 (1994).

Ruat et al.; Calcium sensing receptor: Molecular cloning in rat and localization to nerve terminals; PNAS 92:3161-3165 (1995).

Ruat et al.;Cloned and expressed rat CA2+ sensing receptor; J. Biol. Chem., 271:5972-5975 (1996).

Pollak et al.; Mutations in the human CA2+ sensing receptor gene cause familial hypocalciuric hypercalcemia and neonatal severe hyperparathyroidism, Cell, 75:1297-1303 (1993).

Chattopadhyay et al.; The calcium-sension receptor: A window into the physiology and pathophysiology of mineral ion metabolism; Endocrine 17(4):289-307 (1996).

Gavela et al.; Preparacion de derivados acetilenicos y alenicos de 2-indolilmetilaminas y resultdos preliminares de su estudio como inhibidores selectivos para las monoaminooxidasaas AYB; 82:129-120 (1986).

Nogradi, Thomas; Untersuchungen uber rauwolfia-alkaloid-modelle II; 2-substituierte indole, tetrahydrocarbolin und hexadehydro-yohimban-derivate; Monatshefte fur Chemie. Bd. 88(6) 1088-1094 (1957).

6001 Chemical Abstracts, Columbus, Ohio; XP-002161450 (1987).

6001 Chemical Abstracts, Columbus, Ohio; XP-002161408 (1996).

6001 Chemical Abstracts, Columbus, Ohio; XP-002161449 (1986).

6001 Chemical Abstracts, Columbus, Ohio; XP-002161453 (1996).

6001 Chemical Abstracts, Columbus, Ohio; XP-002161448 (1998).

6001 Chemical Abstracts, Columbus, Ohio; XP-002161454 (1998).

6001 Chemical Abstracts, Columbus, Ohio; XP-002161455 (1986).

6001 Chemical Abstracts, Columbus, Ohio; XP-002161456 (1985).

6001 Chemical Abstracts, Columbus, Ohio; XP-002161451 (1958).

6001 Chemical Abstracts, Columbus, Ohio; XP-002161457 (1958).

6001 Chemical Abstracts, Columbus, Ohio; XP-002161464 (1989).

6001 Chemical Abstracts, Columbus, Ohio; XP-002161465 (1989).

6001 Chemical Abstracts, Columbus, Ohio; XP-002161452 (1978).

6001 Chemical Abstracts, Columbus, Ohio; XP-002161458 (1978).

\* cited by examiner

CALCIUM RECEPTOR ACTIVE MOLECULES AND METHOD FOR PREPARING SAME

This application is a 371 of PCT/FR01/01599, filed May 23, 2001 and claims priority to French Patent Application No. 00/06619, filed May 24, 2000.

The present invention relates to compounds having calcimimetic activity. It in particular relates to a novel class of amino compounds, to the preparation thereof, to the pharmaceutical compositions comprising them and to the use thereof as a modulator of the activity of $(Ca^{2+})_e$ and $(Mg^{2+})_e$ ion receptors or CaSR, for Calcium Sensing Receptor, and as a medicinal product preferably intended for the treatment of physiological disorders or diseases involving modulation of CaSR activity.

The calcimimetic activity corresponds to the ability to produce or induce biological responses observed through variations in the concentration of extracellular calcium ions $(Ca^{2+})_e$ and extracellular magnesium ions $(Mg^{2+})_e$.

$(Ca^{2+})_e$ and $(Mg^{2+})_e$ ions play a major role in the body since they regulate calcium homeostasis on which the vital functions of the body depend. Thus, hypercalcemia, that is to say conditions in which $(Ca^{2+})_e$ ions are below the mean threshold, have a major effect on many functions, such as cardiac, renal or intestinal functions. They deeply affect the central nervous system (Chattopadhyay et al. *Endocr. Review*, 1998).

CaSRs are proteins which are sensitive to $(Ca^{2+})_e$ and $(Mg^{2+})_e$ ions, and are present in the parathyroid and thyroid glands, the kidney, the intestine, the lungs, bone cells, the brain, the spinal cord, the pituitary gland, the stomach and keratinocytes (Brown et al, *Nature*, 1993; Ruat et al, *Proc. Natl. Acad. Sci.*, USA, 1995; Brown et al, *Ann. Rev. Med.*, 1998). These proteins are encoded by a single gene isolated from various animal species. They belong to the family of G protein-coupled receptors with seven transmembrane domains, and exhibit structural homologies with metabotropic glutamate receptors, $GABA_R$ receptors, and hypothetical pheromone and taste receptors. Activating or inhibitory mutations of the genes in humans are responsible for extremely serious genetic diseases which cause hypocalcemia or hypercalcemia (Pollack et al, *Cell*, 1993; Pollack et al, *Nature Genetic*, 1994; Brown et al, *Ann. Rev. Med.*, 1998). The functions associated with the expression of these proteins in tissues are not yet all known and are the subject of a very great deal of research activity, particularly with regard to the CaSRs present in the parathyroid and thyroid glands, the kidney, the intestine, the spinal cord, the brain and bone cells.

In the parathyroid gland, the CaSRs modulate the secretion of parathyroid hormone (PTH), which is the main regulator of calcium homeostasis: an increase in $(Ca^{2+})_e$ ions in the serum will activate the CaSRs present on the cells of the parathyroid gland and decrease secretion of the PTH hormone.

The complementary DNA encoding rat CaSR has been isolated from a rat striatum cDNA library (Ruat et al, *Proc. Natl. Acad. Sci.*, 1995). This receptor is identical, in terms of its amino acid sequence, to that expressed in the other tissues. Transfected Chinese hamster ovary (CHO) cells expressing rat CaSR (CHO(CaSR)) have been characterized and the chemical signals (second messengers) induced by activation of this receptor have been analyzed. Thus, a biochemical test for measuring the accumulation of tritiated inositol phosphates, [³H]IPs, in response to activation of the receptor has been developed (Ruat et al, *J. Biol. Chem.*, 1996; Ferry et al, *Biochem. Biophys. Res. Common.*, 1997).

It has been shown that $Ca^{2+}$ and $Mg^{2+}$ ions, but also $Ba^{2+}$ ions, within millimolar concentration ranges, stimulate CaSRs. Activation of CaSRs might be induced in the brain by β-amyloid peptides, which are involved in neurodegenerative diseases such as Alzheimer's disease (Ye et al, *J. Neurosci. Res.*, 1997).

Disturbance of CaSR activity is associated with biological disorders such as primary and secondary hyperparathyroidism, osteoporosis, cardiovascular, gastrointestinal, endocrine and neurodegenerative diseases, or certain cancers in which $(Ca^{2+})_e$ ions are abnormally high.

Secondary hyperparathyroidism is observed in chronic renal failure and is characterized by hyperplasia of the parathyroid glands and an increase in circulating PTH. The renal failure is also accompanied by renal osteodystrophy, which is characterized by bone disorders with a very considerable or poor renewal of the bone mass (osteitis fibrosa, osteomalacia).

Osteoporosis is a multifactor disease which depends in particular on age and sex. While menopausal women are very greatly affected, osteoporosis is increasingly proving to be a problem in elderly men, and, for the moment, no really satisfactory treatments exist. Its social cost may become even heavier in the years to come, particularly in our European society where life expectancy is becoming longer. Osteoporosis is currently treated with estrogens, calcitonin or biphosphonates which prevent bone resorption without stimulating bone growth. More recent data demonstrate that intermittent increases in PTH or in derivatives thereof are effective in the treatment of osteoporosis and make it possible to remodel bone by stimulating bone formation (Whitfield et al., 1999). This new therapeutic approach for treatment of osteoporosis appears to be very advantageous, although major problems are associated with the use of PTH hormone, such as the route of injection, but also the appearance of tumors, observed recently during clinical trials in humans. Intermittent secretion of endogenous PTH can be obtained by blocking the calcium receptor. The blocking of PTH secretion with CaSR agonists may be followed by a rapid increase in PTH (rebound effect), which is then beneficial in the treatment of osteoporosis.

The search for selective ligands for CaSRs has led the company NPS to develop two main types of family of organic compounds, namely polyamines such as NPS 019 (3), and arylalkylamines, the most well known representative of which, to date, is NPS-R-568 (2).

The compound NPS-R-568 (2), an allosteric ligand of the CaSR, belongs to the first family of small size (M<600) organic molecules which interact with this receptor. This arylalkylamine has developed from the structure of Fendilin (1), a potent activator of the CaSR of the parathyroid gland.

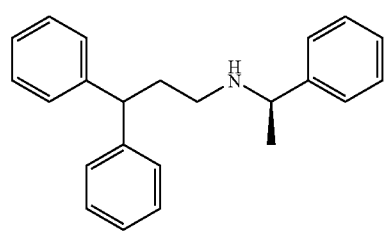

Fendilin

1

-continued

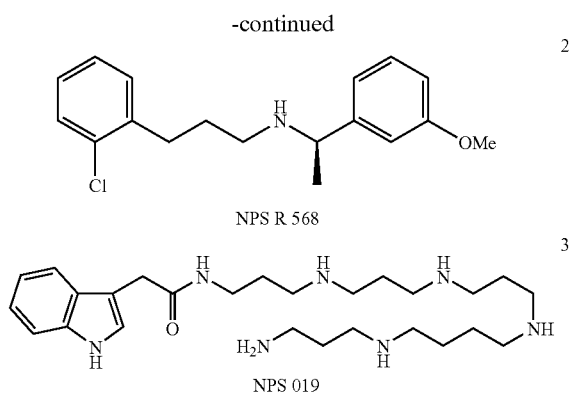

NPS R 568

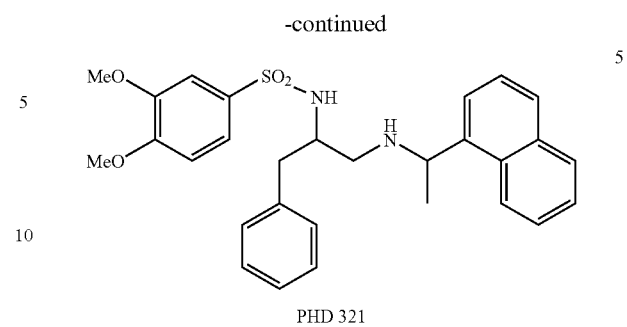

PHD 321

The agent NPS-R-568 reduces or eliminates osteitis fibrosa in rats (Wada et al, *Kidney International*, 1998) and reduces PTH concentrations in patients (men) suffering from chronic renal failure (Antansen et al, Kidney International, 1998). This compound has been successfully used orally to lower concentrations of PTH and of free serum $Ca^{2+}$ ions in menopausal women suffering from primary hyperparathyroidism (Silverborg et al, *New Engl. J. Med.*, 1997). In another study, the compound NPS-R-568 made it possible to reduce by between 20–50% the cell proliferation observed in the parathyroid gland in a rat model reproducing chronic renal failure (Wada et al, *J. Clin. Invest.*, 1997). These studies demonstrate that a calcimimetic compound which is active with respect to the calcium receptor present on the parathyroid gland may be considered to be an advantageous therapeutic tool for treating certain forms of primary and secondary hyperparathyroidism.

During clinical trials (phase I–II), the company NPS Pharmaceutical observed a low bioavailability of the compound NPS-R-568 and also varying clinical effects, depending on the individuals, which might result from polymorphism of the gene encoding the CaSR in humans (Nemeth et al, *Trends Endoc. Metab*, 1999). In addition, during experimental trials in rats, the compound NPS R-467, a compound with a structure similar to NPS-R-568, proved to be more selective with respect to the receptors of the parathyroid compared with those of the thyroid gland. This selectivity can be explained by tissue-related differences, which suggest that calcimimetic molecules specific for a tissue may be synthesized and may be of considerable clinical importance.

In parallel, the preparation and the calcimimetic activity of arylalkyl-1,2-diamines having the general structure described below (4), and among which the compound PHD 321 (5) constitutes one of the most active products, have been reported.

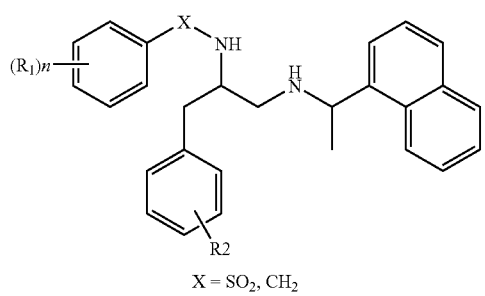

X = SO₂, CH₂

The complete lack of clinically available calcimimetic molecules, and the problems encountered in phase I–II for the first generation calcimimetics underline the need to find novel calcimimetic molecules.

In this invention, the molecules synthesized have advantages compared with the compound NPS-R-568 and with the compound NPS 019 since their structure reveals several sites of interaction with the CaSR or with its transduction system.

The present invention therefore relates to the compounds of the following general formula I:

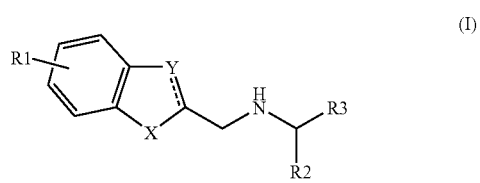

(I)

in which:

the group X represents a group —NR4, —CH=N— or —CHR5-NR4-, the group Y represents an oxygen or sulfur atom or a group —CR5, —CHR5, —CR5=CR6-, —CHR5-CHR6- or NR, on the condition that, when the group X represents the group —CH=N— or —CHR5-NR4-, the group Y represents an oxygen or sulfur atom or the group NR, —CR5 or —CHR5, the group R represents a hydrogen atom or an alkyl, aryl or aralkyl group, the groups R1, R5 and R6, which may be identical or different, each represents a hydrogen or halogen atom or an alkyl or alkoxy group, the group R2 represents a hydrogen atom or an alkyl group, the group R3 represents an aryl group, and the group R4 represents a hydrogen atom, or an alkyl, aryl, aralkyl, alkylsulfonamide, arylsulfonamide or aralkylsulfonamide group, and their salt with a pharmaceutically acceptable acid.

Advantageously, the compounds according to the invention are represented by the following general formula II:

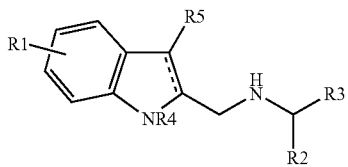

in which:

the groups R1 and R5, which may be identical or different, each represent a hydrogen or halogen atom or an alkyl or alkoxy group, the group R2 represents a hydrogen atom or an alkyl group, the group R3 represents an aryl group, and the group R4 represents a hydrogen atom or an alkyl, aryl, aralkyl, alkylsulfonamide, arylsulfonamide or aralkylsulfonamide group.

Even more advantageously, the group R3 represents a phenyl or naphthyl group which may or may not be substituted.

Examples of advantageous compounds according to the invention are those having the formula III:

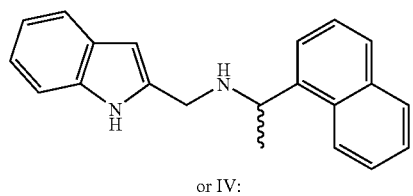

or IV:

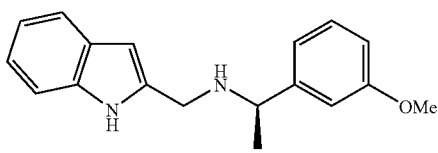

For the purpose of the invention, the term "pharmaceutically acceptable acid" is intended to mean any nontoxic acid, including organic and inorganic acids. Such acids include acetic, benzenesulfonic, benzoic, citric, ethanesulfonic, fumaric, gluconic, glutamic, hydrobromic, hydrochloric, lactic, maleic, malic, mandelic, methanesulfonic, mucic, nitric, pamoic, pantothenic, phosphoric, succinic, sulfuric, tartaric and para-toluenesulfonic acid. Hydrochloric acid is particularly preferred.

For the purpose of the present invention, the term "alkyl group" is intended to mean any linear or branched, substituted or unsubstituted, $C_1$–$C_6$ alkyl group, in particular a methyl group.

For the purpose of the present invention, the term "alkoxy group" is intended to mean any alkoxy group having 1 to 6 linear or branched, substituted or unsubstituted, carbon atoms, in particular the group $OCH_3$.

For the purpose of the present invention, the term "aryl group" is intended to mean one or more aromatic rings having 5 to 8 carbon atoms, which may be joined or fused, and substituted or unsubstituted. In particular, the aryl groups may be phenyl or naphthyl groups and the substituents may be halogen atoms, alkoxy groups as defined above, alkyl groups as defined above or a nitro group.

For the purpose of the present invention, the term "aralkyl group" is intended to mean any aryl group as defined above, linked via an alkyl group as defined above. In particular, an aralkyl group is a benzyl group.

For the purpose of the present invention, the term "alkylsulfonamide group" is intended to mean any alkyl group as defined above, linked via a sulfonamide group.

For the purpose of the present invention, the term "arylsulfonamide group" is intended to mean any aryl group as defined above, linked via a sulfonamide group. In particular, an arylsulfonamide group is the group;

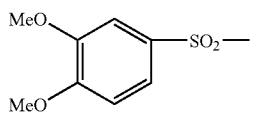

For the purpose of the present invention, the term "aralkylsulfonamide group" is intended to mean any aralkyl group as defined above, linked via a sulfonamide group.

The compounds according to the invention all possess an asymmetric center and can therefore exist in the form of optical isomers. The present invention also comprises these isomers, either separately or as a mixture.

The present invention also relates to the method of preparing these compounds.

This method in particular comprises the steps of:

a) transformation of the carboxylic acid of the following general formula VIII:

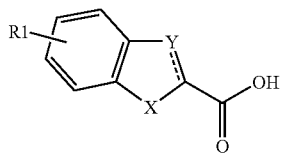

in which:

the group X represents a group —NR4, —CH=N— or —CHR5-NR4-, the group Y represents an oxygen or sulfur atom or a group NR, —CR5, —CHR5, —CR5=CR6- or —CHR5-CHR6-, on the condition that, when the group X represents the group —CH=N— or —CHR5-NR4-, the group Y represents an oxygen or sulfur atom or a group NR, —CR5 or —CHR5, the group R represents a hydrogen atom or an alkyl, aryl or aralkyl group, the groups R1, R5 and R6, which may be identical or different, each represent a hydrogen or halogen atom or an alkyl or alkoxy group, and the group R4 represents a hydrogen atom or an alkyl, aryl, aralkyl, alkylsulfonamide, arylsulfonamide or aralkylsultonamide group, into acyl chloride of the following general formula VI:

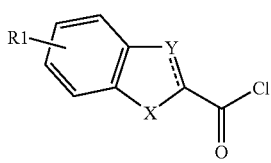

in which:

the group X represents a group —NR4, —CH=N— or —CHR5-NR4-, the group Y represents an oxygen or sulfur atom or a group NR, —CR5, —CHR5, —CR5=CR6- or —CHR5-CHR6-, on the condition that, when the group X represents the group —CH=N— or —CHR5-NR4-, the group Y represents an oxygen or sulfur atom or a group NR, —CR5 or —CHR5, the group R represents a hydrogen atom or an alkyl, aryl or aralkyl group, the groups R1, R5 and R6, which may be identical or different, each represent a hydrogen or halogen atom or an alkyl or alkoxy group, and the group R4 represents a hydrogen atom or an alkyl, aryl, aralkyl, alkylsulfonamide, arylsulfonamide or aralkylsulfonamide group, advantageously by reaction with a thionyl chloride.

b) reaction between the acyl chloride of general formula VI and an amine of the following general formula VII:

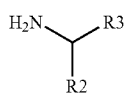

in which:

the group R2 represents a hydrogen atom or an alkyl group, and the group R3 represents an aryl group, so as to obtain the amide of the following general formula V:

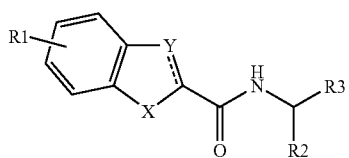

in which:

the group X represents a group —NR4, —CH=N— or —CHR5-NR4-, the group Y represents an oxygen or sulfur atom or a group NR, —CR5, —CHR5, —CR5=CR6- or —CHR5-CHR6-, on the condition that, when the group X represents the group —CH=N— or —CHR5-NR4-, the group Y represents an oxygen or sulfur atom or a group NR, —CR5 or —CHR5, the group R represents a hydrogen atom or an alkyl, aryl or aralkyl group, the groups R1, R5 and R6, which may be identical or different, each represent a hydrogen or halogen atom or an alkyl or alkoxy group, the group R2 represents a hydrogen atom or an alkyl group, the group R3 represents an aryl group, and the group R4 represents a hydrogen atom or an alkyl, aryl, aralkyl, alkylsaufonamide, arylsulfonamide or aralkylsulfonamide group.

c) Reduction of the amide of general formula V, advantageously with $LiAlH_4$, in a compound of general formula I.

The carboxylic acids of general formula VIII and the amines of general formula VII are readily available commercially.

The simplicity of this synthesis and its very good yield make it possible to introduce a large variety of substituents R, R1, R2, R3, R4, R5 and R6 onto the compound of general formula I.

The use, in the method of synthesis, of an optically pure isomer of the amine of general formula VII allows the synthesis of an optically pure compound of general formula I.

The present invention also relates to the amides of the following general formula V:

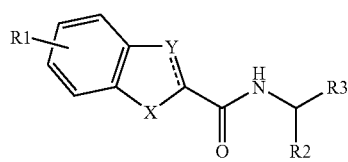

in which:

the group X represents a group —NR4, —CH=N— or —CHR5-NR4-, the group Y represents an oxygen or sulfur atom or a group NR, —CR5, —CHR5, —CR5=CR6- or —CHR5-CHR6-, on the condition that, when the group X represents the group —CH=N— or —CHR5-NR4-, the group Y represents an oxygen or sulfur atom or a group NR, —CR5 or —CHR5, the group R represents a hydrogen atom or an alkyl, aryl or aralkyl group, the groups R1, R5 and R6, which may be identical or different, each represent a hydrogen or halogen atom or an alkyl or alkoxy group, the group R2 represents a hydrogen atom or an alkyl group, the group R3 represents an aryl group, and the group R4 represents a hydrogen atom or an alkyl, aryl, aralkyl, alkylsulfonamide, arylsulfonamide or aralkylsulfonamide group, and their salts with a pharmaceutically acceptable acid.

These amides are a reaction intermediate of the synthesis of the compound of general formula I.

The amides according to the invention all have an asymmetric center and may therefore exist in the form of optical isomers. The present invention also comprises the isomers, either separately or as a mixture.

The present invention also relates to the pharmaceutical compositions comprising, as active principle, one of the compounds defined above, and a suitable excipient. These compositions can be formulated for administration to mammals, including humans. The dosage varies depending on the treatment and depending on the condition in question. These compositions are prepared so as to be administrable by the digestive or parenteral route.

In the pharmaceutical compositions of the present invention for oral, sublingual, subcutaneous, intramuscular, intravenous, transdermal, local or rectal administration, the active ingredient can be administered in unit forms for administration, mixed with conventional pharmaceutical carriers, to animals or to humans. Suitable unit forms for administration comprise the forms for oral administration, such as tablets, gelatin capsules, powders, granules and oral solutions or suspensions, the forms for sublingual and buccal administration, the forms for subcutaneous, intramuscular, intravenous, intranasal or intraoccular administration and the forms for rectal administration.

When a solid composition is prepared in the form of tablets, the main active ingredient is mixed with a pharmaceutical vehicle such as gelatin, starch, lactose, magnesium stearate, talc, gum arabic and the like. The tablets may be coated with sucrose or with other suitable materials, or they may be treated in such a way that they have a prolonged or delayed activity and they continuously release a predetermined amount of active principle.

A preparation in gelatin capsules is obtained by mixing the active ingredient with a diluent and pouring the mixture obtained into soft or hard gelatin capsules.

A preparation in the form of a syrup or an elixir may contain the active ingredient together with a sweetener, an antiseptic, and also a taste enhancer and a suitable coloring agent.

The water-dispersible powders or granules may contain the active ingredient mixed with dispersing agents or wetting agents, or suspending agents, and with flavor correctors or sweeteners.

For rectal administration, suppositories are used which are prepared with binders which melt at rectal temperature, for example cocoa butter or polyethylene glycols.

For parenteral, intranasal or intraoccular administration, aqueous suspensions, isotonic saline solutions or sterile and injectable solutions which contain pharmacologically compatible dispersing agents and/or wetting agents are used.

The active principle may also be formulated in the form of microcapsules, optionally with one or more carrier additives.

The present invention also relates to the use of these compounds, and of the pharmaceutical compositions comprising them, as a modulator of CaSR activity.

The CaSR can be found in the parathyroid gland, the thyroid, bone cells, the stomach, the lung, the kidney, pituitary gland, the brain, the hypothalamus, the olfactory areas or the hippocampus.

The compounds according to the present invention are preferably more selective, in their use, with respect to the receptors of the parathyroid compared with those of the thyroid gland.

The compounds according to the invention, and the pharmaceutical compositions comprising them, may be used as a medicinal product, in particular for the treatment of physiological disorders or diseases associated with disturbances of CaSR activity. Even more particularly, these physiological disorders or diseases of the type including primary or secondary hyperparathyroidism, osteoporosis, cardiovascular, gastrointestinal, endocrine or neurodegenerative diseases or certain cancers in which $(Ca^{2+})_e$ ions are abnormally high. The secondary hyperparathyroidism is more particularly observed in chronic renal failure.

The following example of synthesis of compounds according to the invention is given by way of nonlimiting illustration of the invention.

Synthesis of
(R)-N-[1-(1-naphthyl)ethyl]indole-2-carboxamide 7 equivalents of thionyl chloride (0.760 ml; 10.5 mmol) and 0.020 ml of N,N-dimethylformamide (DMF) are successively added, at ambient temperature, under argon, to a solution of indole-2-carboxylic acid (242 mg; 1.5 mmol) in 10 ml of chloroform. After stirring overnight at 30° C., the mixture is evaporated to dryness to give a corresponding acid chloride in the form of an oily yellow residue. The latter is dissolved in 10 ml of chloroform and then 1.5 equivalents of triethylamine (0.315 ml; 2.25 mmol) and 1.5 equivalents of (R)-1-(1-naphthyl)ethylamine (0.360 ml; 2.25 mmol) are added. The solution is stirred for 2 hours at ambient temperature before being concentrated and then purified on a silica column (eluant: heptane/ethyl acetate: 4/1). 340 mg (1.08 mmol; 72%) of the amide are isolated in the form of a yellow solid.

Mass spectrometry (ES): m/z: 315 $[M+H]^+$

Synthesis of (R)-N-[(indole-2-yl)methyl]-N-[1-(1-naphthyl)ethyl]amine.HCl (PHD 337-R)

A solution of aluminum chloride, $AlCl_3$ (213 mg; 1.6 mmol), in 4 ml of distilled tetrahydrofuran (THF) is added, at ambient temperature, under argon, to a solution of lithium aluminum hydride, $LiAlH_4$ (60 mg; 1.6 mmol), in 2 ml of distilled THF. The solution is stirred for 45 minutes at ambient temperature before introducing the amide (252 mg; 0.80 mmol) in steps. The reaction medium is then heated to 60° C. After 6 hours of reaction, a further two equivalents of $LiAlH_4$ (60 mg; 1.6 mmol) are added. The reaction is left overnight at 60° C. and then, after cooling, the medium is hydrolyzed by slowly adding aqueous 10% THF. The mixture is then treated with a molar sodium hydroxide solution before being extracted 3 times with ethyl ether. The organic phase is dried over sodium sulfate, evaporated and purified on a silica column (eluant: heptane/ethyl acetate: 60/10). 200 mg (0.66 mmol; 83%) of a yellow oil are isolated. The free amine is then transformed into its hydrochloride by treatment in chloroform with a saturated solution of hydrochloric acid in methanol.

Melting point: 204° C.
Mass spectrometry (ES): m/z: 301 $[M+H]^+$
Optical rotation: $[\alpha]^{20}_D = +25.0°$ (c 0.4, $CHCl_3$)

Activity on Transfected Cells Expressing the $[Ca^{2+}]_e$ Ion Sensing Receptor

The calcimimetic activity of the compounds was estimated by measuring the accumulation of tritiated inositol phosphates, induced by 10 µM of each of the compounds in the presence of 2 mM of $Ca^{2+}$, in CHO(CaSR) cells (Ferry et al, *Biochem Biophys Res Commun*, 1997).

This activation was compared with that induced by the compound NPS-R-568, a reference calcimimetic used at a concentration of 10 µM (Table 1) (Ferry et al, *Biochem Biophys Res Commun*, 1997; Nemeth et al, *Proc Natl Acad Sci USA*, 1997).

The compounds PHD 337, PHD 337R and PHD 356, used at a concentration of 10 µM, exhibit an activity ranging from 90 to 100% of that obtained with 10 mM of $Ca^{2+}$, comparable to that of the compound NPS-R-568 at the same concentration (Table 1). It should be noted (Table 2) that the compounds PHD 337 and PHD 337R or the compound PHD 356 at 1 μM exhibit an activity which is 50% greater than that of calcium (10 mM), whereas the compound PHD 363 is less active at this same concentration, suggesting that the group R1 on the phenyl ring has an important role.

TABLE 1

Accumulation of tritiated inositol phosphates in CHO (CaSR) cells, induced by the PHD/AK compounds and by the calcimimetic compound NPS-R-568

| Compound- (10 μM) | Empirical formula- Molar mass (melting point) | Structure | Accumulation of ($^3$H)-IP % of the 10 mM Ca$^{2+}$ response ± S.E. |
|---|---|---|---|
| NPS R-568 | $C_{18}H_{22}ClNO·HCl$ 340,29 | 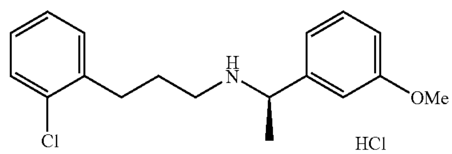 | 106 ± 15 |
| PHD 337 | $C_{21}H_{20}N_2·2HCl$ 373,32 | 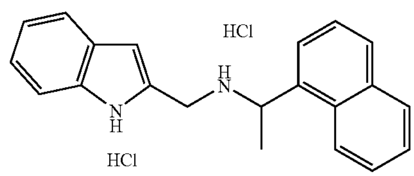 | 103 ± 6 |
| PHD 337-R | $C_{21}H_{20}N_2·2HCl$ 373,32 | 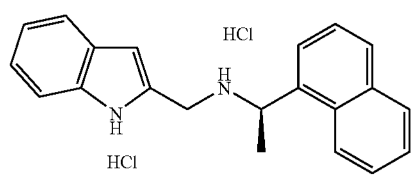 | 117 ± 5 |
| PHD 337-S | $C_{21}H_{20}N_2·2HCl$ 373,32 | 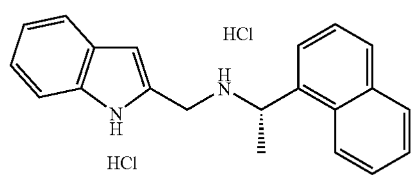 | 32 ± 5 |
| PHD 356 | $C_{29}H_{20}N_2O·2HCl$ 353,29 | 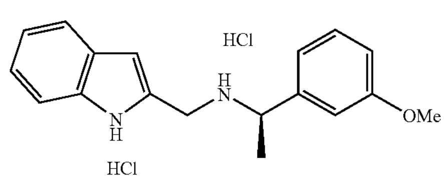 | 105 ± 15 |

TABLE 1-continued

Accumulation of tritiated inositol phosphates in CHO (CaSR) cells, induced by the PHD/AK compounds and by the calcimimetic compound NPS-R-568

| Compound- (10 µM) | Empirical formula- Molar mass (melting point) | Structure | Accumulation of ($^3$H)-IP % of the 10 mM Ca$^{2+}$ response ± S.E. |
|---|---|---|---|
| PHD 359 | $C_{22}H_{22}N_2O \cdot 2HCl$ 403,34 | 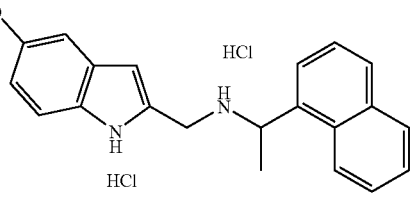 | 55 ± 5 |
| PHD 361 | $C_{21}H_{19}FN_2 \cdot 2HCl$ 391,32 | 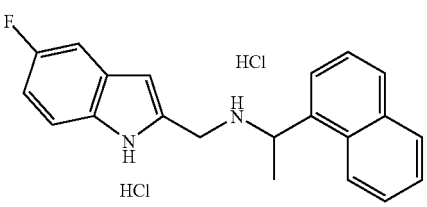 | 87 ± 7 |
| PHD 363 | $C_{21}H_{19}ClN_2 \cdot 2HCl$ 407,77 | 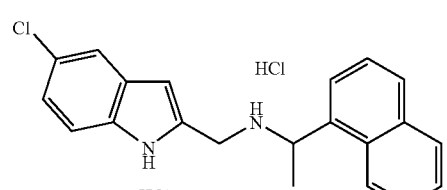 | 60 ± 1 |
| PHD 368 | $C_{21}H_{22}N_2 \cdot 2HCl$ 375,34 | 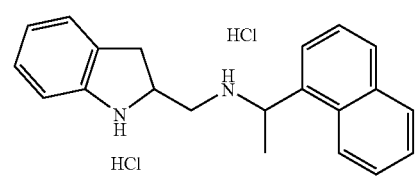 | 77 ± 1 |
| PHD 338 | $C_{29}H_{28}N_2O_4S \cdot 2HCl$ 537,08 | 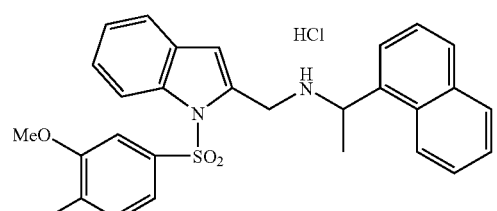 | 54 ± 5 |
| AK 43 | $C_{22}H_{22}N_2 \cdot 2HCl$ 350,89 | 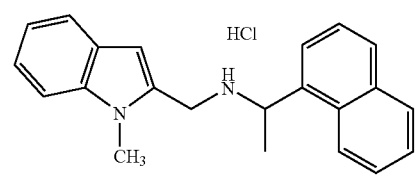 | 79 ± 13 |

The calcimimetic activity of the PHD/AK compounds is compared with that of a reference compound, NPS-R-568, used at the same concentration and under the same experimental conditions. This activity is expressed as a percentage of the activity of 10 mM of $Ca^{2+}$. The means±standard errors of the means of 2 to 5 independent manipulations are indicated. The experiments were carried out in the presence of 2 mM of $Ca^{2+}$.

4.2 Specificity of the Activity of These Molecules

The PHD molecules, used at a concentration of 10 µM, produce little or no accumulation of [$^3$H]IP in control CHO(WT$^+$) cells, which suggests their specificity of action with respect to the CaSR (Table 3). The CHO(WT$^+$) cells were transfected with the plasmid alone and do not express the CaSR.

TABLE 2

Accumulation of tritiated inositol phosphates in CHO (CaSR) cells, induced by the PHD compounds at 1 µM

| Compound-(10 µM) | Empirical formula- Molar mass (melting point) | Structure | Accumulation of ($^3$H)-IP % of the 10 mM $Ca^{2+}$ response ± S.E. |
|---|---|---|---|
| PHD 337 | $C_{21}H_{20}N_2 \cdot 2HCl$ 373,32 | 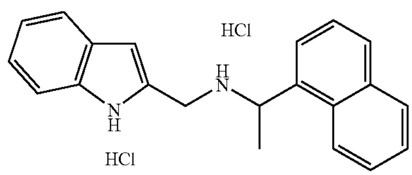 | 69 ± 9 |
| PHD 337-R | $C_{21}H_{20}N_2 \cdot 2HCl$ 373,32 | 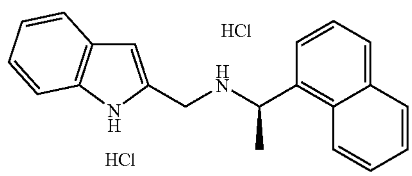 | 73 ± 10 |
| PHD 337-S | $C_{31}H_{20}N_2 \cdot 2HCl$ 373,32 | 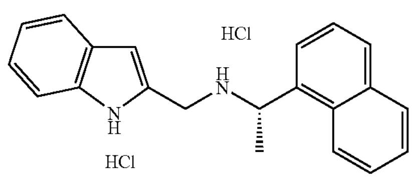 | 3 ± 2 |
| PHD 356 | $C_{29}H_{20}N_2O \cdot 2HCl$ 353,29 | 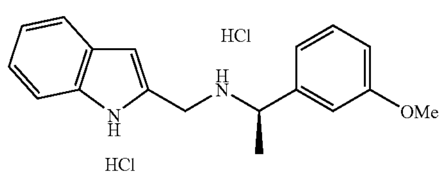 | 76 ± 1 |
| PHD 363 | $C_{21}H_{19}ClN_2 \cdot 2HCl$ 407,77 | 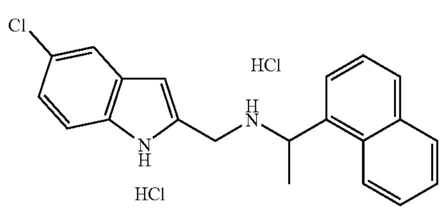 | 6 ± 3 |

The accumulation of tritiated inositol phosphates is expressed as a percentage of the basal level observed in the presence of 2 mM $Ca^{2+}$ (100%) in CHO ($WT^+$) or CHO (CaSR) cells.

TABLE 3

Accumulation of tritiated inisotol phosphates in the CHO (CaSR) and CHO (WT*) cells, induced by the PHD/AK compounds and the calcimimetic compound NPS-R-568

| Compound- (10 μM) | Structure | Accumulation of ($^1$H)-IP % of basal level | |
|---|---|---|---|
| | | CHO (WT*) | CHO (CaSR) |
| NPS R-568 | 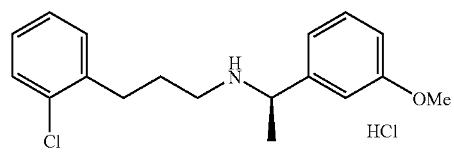 | 110 ± 9 | 454 ± 33 |
| PHD 337 | 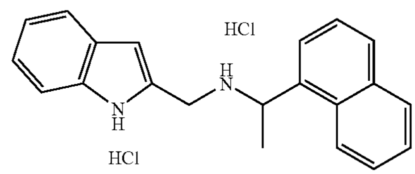 | 147 ± 14 | 444 ± 101 |
| PHD 337-R | 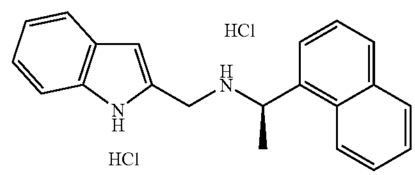 | 130 ± 9 | 588 ± 129 |
| PHD 337-S | 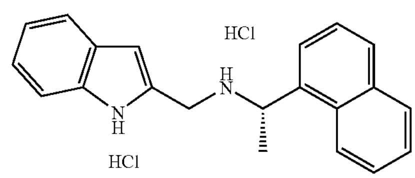 | 132 ± 1 | 225 ± 7 |
| PHD 356 | 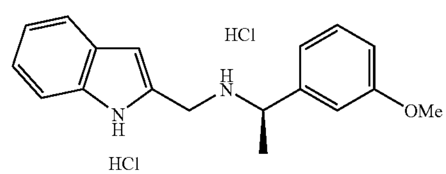 | 151 ± 7 | 482 ± 58 |
| PHD 359 | 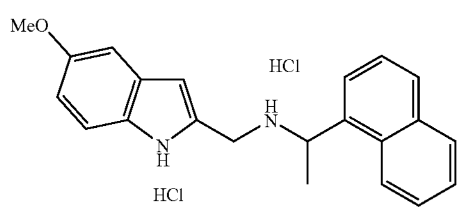 | 117 ± 8 | 303 ± 42 |

TABLE 3-continued

Accumulation of tritiated inisotol phosphates in the CHO (CaSR) and CHO (WT*) cells, induced by the PHD/AK compounds and the calcimimetic compound NPS-R-568

| Compound- (10 μM) | Structure | Accumulation of ($^1$H)-IP % of basal level | |
|---|---|---|---|
| | | CHO (WT*) | CHO (CaSR) |
| PHD 361 | 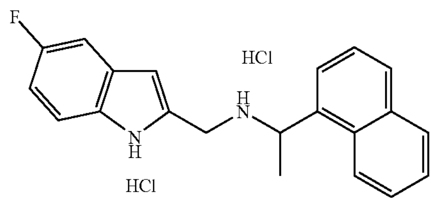 | 133 ± 3 | 420 ± 70 |
| PHD 363 | 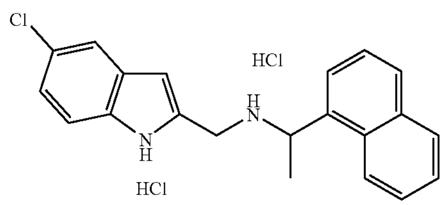 | 125 ± 12 | 325 ± 67 |
| PHD 368 | 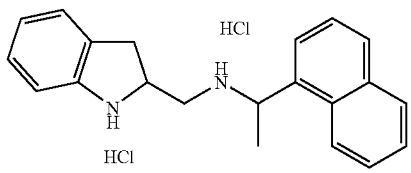 | 126 ± 6 | 388 ± 85 |
| PHD 338 | 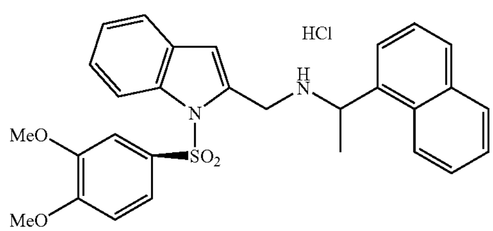 | 111 ± 10 | 202 ± 9 |
| AK 43 | 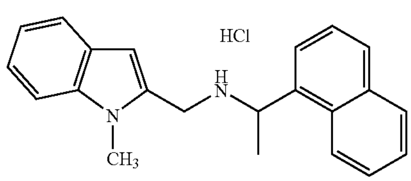 | 109 ± 2 | 401 ± 16 |

The invention claimed is:

1. A compound of the following formula I:

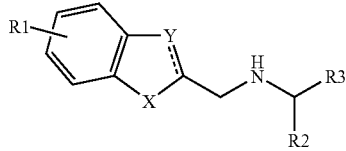

in which:

the group X represents a group

the group Y represents a group

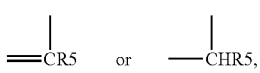

the groups R1 and R5, which may be identical or different, each represent a hydrogen or halogen atom or an alkyl or alkoxy group, the group R2 represents a hydrogen atom or an alkyl group, the group R3 represents an aryl group, and the group R4 represents a hydrogen atom or an alkyl, aryl, aralkyl, alkylsulfonamide, arylsulfonamide or aralkylsulfonamide group, and its salt with a pharmaceutically acceptable acid, in the form of a racemic mixture or of its optically pure isomer, and with the exception of compounds, which have the following formulae:

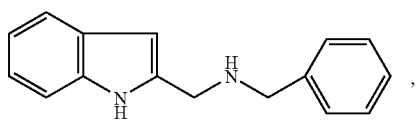

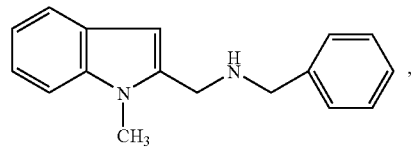

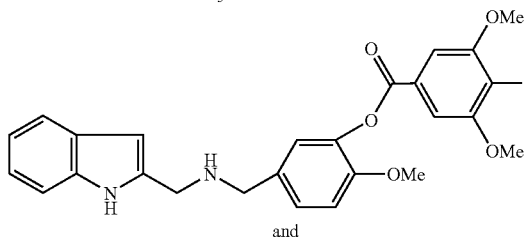

and

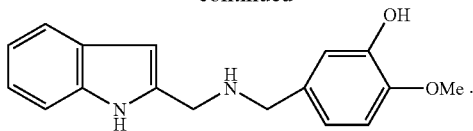

2. The compound of claim 1, wherein the compound is represented by the following formula III:

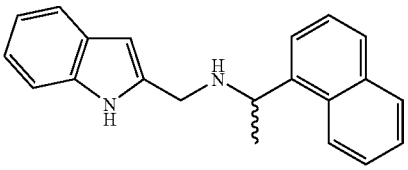

and its salt with a pharmaceutically acceptable acid, in the form of a racemic mixture or of its optically pure isomer.

3. The compound of claim 1, wherein the compound is represented by the following formula IV:

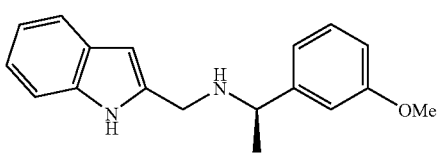

and its salt with a pharmaceutically acceptable acid.

4. A method for preparing the compound of claim 1, comprising reducing an amide of the following formula V:

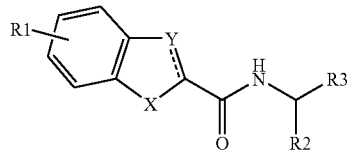

in which:

the group X represents a group

the group Y represents a group

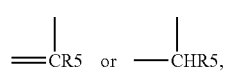

the groups R1 and R5, which may be identical or different, each represent a hydrogen or halogen atom or an alkyl or alkoxy group, the group R2 represents a hydrogen atom or an alkyl group, the group R3 represents an aryl group, and the group R4 represents a hydrogen atom or an alkyl, aryl, aralkyl, alkylsulfonamide, arylsulfonamide or aralkylsulfonamide group, and with the exception of the compounds, which have the following formula:

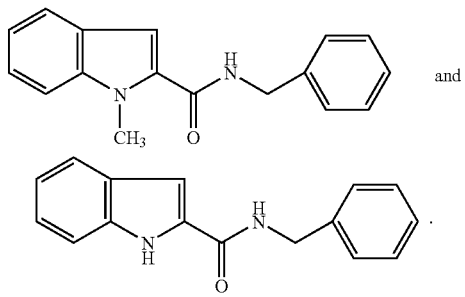

and

5. The method of claim 4, wherein the method further comprises reacting:

(A) an acyl chloride of the following formula VI:

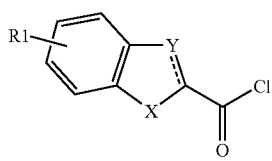

in which:

the group X represents a group

the group Y represents a group

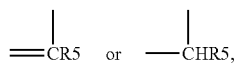

the groups R1 and R5, which may be identical or different, each represent a hydrogen or halogen atom or an alkyl or alkoxy group, and the group R4 represents a hydrogen atom or an alkyl, aryl, aralkyl, alkylsulfonamide, arylsulfonamide or aralkylsulfonamide group, with (B) an amine of the following formula VII:

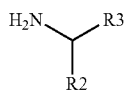

in which:

the group R2 represents a hydrogen atom or an alkyl group, and the group R3 represents an aryl group;

so as to obtain the amide of general formula V, wherein the following groups are substituted or unsubstituted: alkyl, alkoxy, aryl, aralkyl, alkylsulfonamide, arylsulfonamide, and aralkylsulfonamide.

6. The method of claim 5, wherein the method further comprises reacting a carboxylic acid of the following formula VIII:

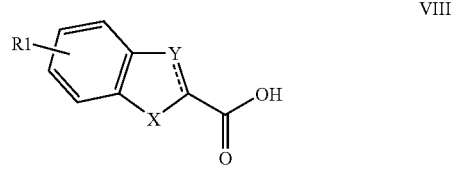

in which:

the group X represents a group

the group Y represents a group

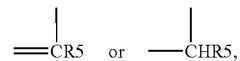

the groups R1 and R5, which may be identical or different, each represent a hydrogen or halogen atom or an alkyl or alkoxy group, and the group R4 represents a hydrogen atom or an alkyl, aryl, aralkyl, alkylsulfonamide, arylsulfonamide or aralkylsulfonamide group;

with a thionyl chloride;

so as to obtain acyl chloride of the formula VI, wherein the following groups are substituted or unsubstituted: alkyl, alkoxy, aryl, aralkyl, alkylsulfonamide, arylsulfonamide, and aralkylsulfonamide.

7. A pharmaceutical composition comprising: (A) a compound of the following formula I:

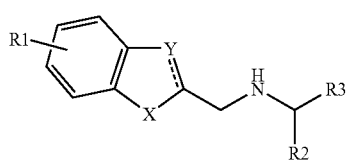

in which:

the group X represents a group

the group Y represents a group

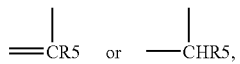

the groups R1 and R5, which may be identical or different, each represent a hydrogen or halogen atom or an alkyl or alkoxy group, the group R2 represents a hydrogen atom or an alkyl group, the group R3 represents an aryl group;

and the group R4 represents a hydrogen atom or an alkyl, aryl, aralkyl, alkylsulfonamide, arylsulfonamide or aralkylsulfonamide group, wherein the following groups are substituted or unsubstituted: alkyl, alkoxy, aryl, aralkyl, alkylsulfonamide, arylsulfonamide, and aralkylsulfonamide; and (B) a suitable pharmaceutical carrier.

8. A pharmaceutical composition comprising the compound of claim 2 and a suitable pharmaceutical carrier.

9. A pharmaceutical composition comprising the compound of claim 3 and a suitable pharmaceutical carrier.

* * * * *

UNITED STATES PATENT AND TRADEMARK OFFICE
CERTIFICATE OF CORRECTION

PATENT NO. : 7,084,167 B2
APPLICATION NO. : 10/296288
DATED : August 1, 2006
INVENTOR(S) : Martial Ruat et al.

It is certified that error appears in the above-identified patent and that said Letters Patent is hereby corrected as shown below:

Col. 1, line 40, "$GABA_R$ should be -- $GABA_B$ --.

Col. 6, line 66 bridging line 67, "alkylsultonamide" should be -- alkylsulfonamide --.

Col. 8, line 8, "alkylsaufonamide" should be -- alkylsulfonamide --.

Col. 16, lines 5 and 6, "$CHO(WT^+)$" should be -- $CHO(WT^*)$ --, both occurrences.

Col. 22, claim 1, line 6 after the last formula, insert: --wherein the following groups are substituted or unsubstituted: alkyl, alkoxy, aryl, aralkyl, alkylsulfonamide, arylsulfonamide, and aralkylsulfonamide.--

Col. 23, claim 4, line 21 after the last formula, insert: --wherein the following groups are substituted or unsubstituted: alkyl, alkoxy, aryl, aralkl, alkylsulfonamide, arylsulfonamide, and aralkylsulfonamide.--

Signed and Sealed this

Twelfth Day of December, 2006

JON W. DUDAS
*Director of the United States Patent and Trademark Office*